United States Patent
Kurth

(10) Patent No.: US 7,401,680 B2
(45) Date of Patent: Jul. 22, 2008

(54) HEARING PROTECTION EARPLUG AND USE OF THE SAME

(75) Inventor: Roland Kurth, La Neuveville (CH)

(73) Assignee: Phonak AG, Staefa (CH)

( * ) Notice: Subject to any disclaimer, the term of this patent is extended or adjusted under 35 U.S.C. 154(b) by 393 days.

(21) Appl. No.: 11/019,637

(22) Filed: Dec. 23, 2004

(65) Prior Publication Data

US 2006/0137934 A1    Jun. 29, 2006

(51) Int. Cl.
*H04R 25/02* (2006.01)
*H04R 1/10* (2006.01)

(52) U.S. Cl. .................. 181/135; 181/126; 181/129; 181/130; 381/322; 381/324; 381/328; 381/329

(58) Field of Classification Search ............. 181/129, 181/130, 135; 381/322, 324, 328, 329
See application file for complete search history.

(56) References Cited

U.S. PATENT DOCUMENTS

| 5,631,965 | A | 5/1997 | Chang et al. | |
|---|---|---|---|---|
| 6,533,062 | B1 | 3/2003 | Widmer et al. | |
| 6,687,377 | B2 | 2/2004 | Voix et al. | |
| 6,819,770 | B2* | 11/2004 | Niederdrank | 381/322 |
| 2002/0080979 | A1* | 6/2002 | Brimhall et al. | 381/72 |
| 2003/0037989 | A1 | 2/2003 | Widmer et al. | |
| 2003/0112990 | A1 | 6/2003 | McIntosh et al. | |
| 2003/0133583 | A1 | 7/2003 | Widmer et al. | |
| 2003/0179894 | A1* | 9/2003 | Saltykov | 381/313 |
| 2006/0034473 | A1* | 2/2006 | Halteren et al. | 381/322 |
| 2006/0042868 | A1* | 3/2006 | Berg et al. | 181/135 |
| 2006/0045299 | A1* | 3/2006 | Haussmann | 381/328 |
| 2006/0140416 | A1* | 6/2006 | Berg | 381/72 |
| 2007/0071265 | A1* | 3/2007 | Leedom et al. | 381/322 |

FOREIGN PATENT DOCUMENTS

| EP | 1 071 307 A1 | 1/2001 |
|---|---|---|
| WO | WO 02/50499 A2 | 6/2002 |

\* cited by examiner

*Primary Examiner*—Lincoln Donovan
*Assistant Examiner*—Jeremy Luks
(74) *Attorney, Agent, or Firm*—David S. Safran

(57) ABSTRACT

A hearing protection earplug having a shell worn at least in part in a user's ear canal, an active unit having an acoustic output transducer and an arrangement for producing output audio signals for said output transducer, and a detachable connection of the active unit to said shell, the shell including a sound passage extending between an outer opening of said shell and an inner sound output opening of said shell and having a valve mechanism which is moveable, upon connecting said active unit to said shell, from a closed position acoustically closing said sound passage into an open position acoustically opening said sound passage, said valve mechanism being biased towards said closed position when said active unit is removed from said shell, and wherein said output transducer is acoustically connected to said sound output opening via said sound passage when said active unit is connected to said shell.

32 Claims, 3 Drawing Sheets

HEARING PROTECTION EARPLUG AND USE OF THE SAME

BACKGROUND OF THE INVENTION

1. Field of the Invention

The invention relates to a hearing protection earplug comprising a removable active unit, to a use of such an earplug and to a method for manufacturing such an earplug. The invention further relates to a hearing protection system comprising an earplug and a plurality of removable active units.

2. Description of Related Art

US 2003/0112990 A1 relates to a hearing protection earplug comprising a customized shell with an outer shape adapted to the inner shape of the user's outer ear and ear canal. The shell comprises a sound passage extending through the earplug, with the outer end of the sound passage being provided with a slit membrane which closes the sound passage whenever engaged by a remote instrument such as a microphone of a measurement device. The shell further comprises a receptacle for an insert member which may be a communication element, i.e. an active unit, comprising a microphone and a speaker, and which may be releasably engaged within the receptacle of the shell. The receptacle communicates with a second sound passage extending through the earplug.

US 2002/0080979 A1 relates to a hearing protection earplug comprising a soft shell, i.e. a shell made of a relatively resilient material which is capable of adapting its outer shape to the inner shape of the user's outer ear and ear canal, into which soft shell an electronic module, i.e. an active unit, may be inserted in a detachable manner for enabling exchange of the soft shell. The electronic module comprises a microphone, a signal processing unit and a speaker for providing for an active hearing protection function.

U.S. Pat. No. 5,631,965 relates to a hearing protection earplug comprising a soft shell and an active unit which is screwed into the shell. The active unit includes a microphone, a signal processing unit and a speaker, with the speaker communicating with a sound passage extending through the shell.

U.S. Pat. No. 6,687,377 B2 relates to a hearing protection earplug comprising a shell with a sound measurement channel which extends through the shell and which terminates at an opening at the outer end of the shell. A remote device such as a sound measurement device may be temporarily inserted into the outer opening of the sound measurement passage.

US 2003/0037989 A1 relates to an earplug comprising a customized shell which is provided with a receptacle into which a hearing aid module comprising a microphone, a signal processing unit and a speaker may be releasably inserted for allowing exchange of the shell. The speaker of the hearing aid module communicates with a sound passage extending through the shell.

It is an object of the invention to provide for a hearing protection earplug which allows for a highly flexible use by enabling the user to select between different functions in a simple and easy manner. It is a further object of the invention to provide for a manufacturing method and a use of such an earplug and for a hearing protection system comprising such an earplug.

SUMMARY OF THE INVENTION

These objects are attained according to the present invention by a hearing protection earplug as defined in claims 1 and 2, respectively, by a use of such a hearing protection earplug as defined in claim 27, by a method for manufacturing such an earplug as defined in claim 30 and by a hearing protection system comprising such an earplug as defined in claim 29.

The invention is beneficial in that the hearing protection earplug can be used, according to the desires of the user, either without the active unit being inserted into the shell, with the hearing protection earplug in this case acting as a passive hearing protection earplug with the sound passage being closed by the valve means, or with the active unit being inserted into the shell, with the hearing protection earplug in this case being provided with additional functionality, such as a selective communication function, i.e. the earplug acting as an active hearing protection device, or an in-situ sound attenuation measurement function, with the active unit being acoustically connected via the opened valve means with the sound passage. The invention also allows for alternatively using active units having different functionality with the same earplug in order to provide for a particularly high flexibility of use. Due to the provision of the acoustic valve means the change between different use modes and hence the handling of the earplug by the user is particularly simple. Further, due to the fact that the active unit can be easily removed from the shell, the earplug is easy to clean. Finally, by manufacturing the shell together with the valve means by an additive layer-by-layer build-up process, the valve means can be implemented in a particularly simple manner without the need of a separate assembly step for mounting the valve means at the shell.

Preferred embodiments of the invention are defined in the dependent claims.

These and further objects, features and advantages of the present invention will become apparent from the following description when taken in connection with the accompanying drawings which, for purposes of illustration only, show several embodiments in accordance with the present invention.

Figure 1A:
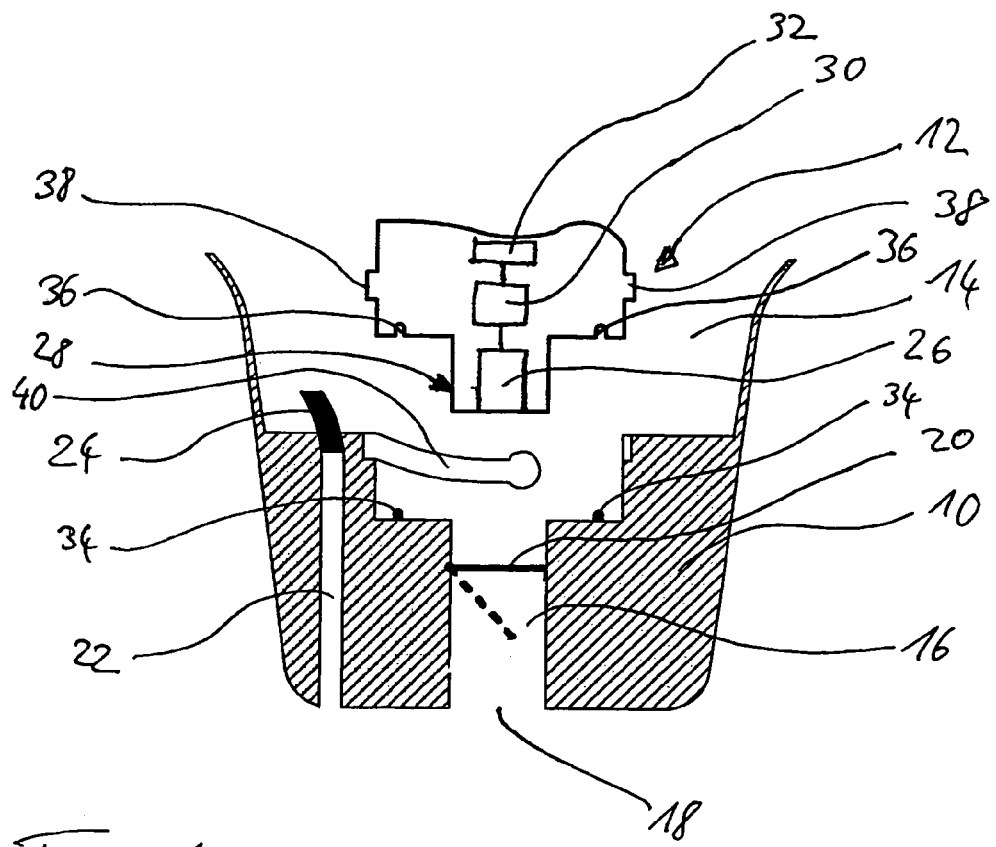
FIGS. 1a and 1b show a schematic side view, partially in cross-section, of the distal end of a first embodiment of a hearing protection earplug according to the invention, wherein the active unit is shown in a condition prior to being fixed within the shell and after having been fixed within the shell, respectively.

The present invention relates to hearing protection earplugs comprising a shell which is adapted to be worn at least in part in a user's ear canal, i.e. at least a distal portion of the shell is to be inserted into the outer part of the user's ear canal in order to provide for an acoustic attenuation of at least 10 dB averaged over the audible frequency range when the earplug is worn by the user, in order to protect the user from excessive levels of ambient sound. The earplug may comprise an acoustic filter for adjusting the desired total acoustic attenuation or for adjusting the frequency dependent acoustic attenuation.

The shell preferably is a hard shell having an elasticity from shore D85 to D65 and preferably is made of polyamide. In order to achieve optimized fit of the shell within the user's outer ear and ear canal, the shell preferably has an outer surface individually shaped according to the measured shape of the user's outer ear and ear canal, i.e. the shell preferably has an individually customized outer shape. The shape of the user's outer ear and ear canal may be determined by direct three-dimensional scanning of the ear canal and the concha or by producing an impression of the ear canal and the concha which subsequently undergoes scanning. The scanning process may be carried out optically, preferably by laser scanning.

The digital data obtained by the scanning process is then used to create the hard shell by an additive or incremental layer-by-layer build up process. Such processes are also known as "rapid prototyping". A preferred additive build-up process is a layer-by-layer laser sintering process of powder material, preferably polyamide powder. Such processes are also known as "selective laser sintering" (SLS). The basic principle therein is the repeated deposition of a thin layer of material on a surface, with the desired sectional shape then being stabilized, i.e. hardened, by laser action. An overview regarding such processes can be found, for example, in US 2003/0133583 A1 or U.S. Pat. No. 6,533,062 B1.

According to the invention, the shell is provided with a sound passage which extends between an outer opening of the shell and an inner sound output opening at the distal end of the shell. Further, the shell comprises valve means which are movable between a closed position in which the valve means acoustically open the sound passage, with the valve means being biased towards the closed position. The shell further is adapted to be detachably connected with an active unit which causes the valve means to move from the closed position into the open position upon engagement between the active unit and the shell. Thereby it is possible to use the earplug as a passive hearing protection earplug with the active unit being removed, or as a hearing protection earplug with added functionality provided by the active unit when connected to the shell.

Preferably, the valve means provides in the closed position for an acoustic attenuation of at least 10 dB averaged over the audible frequency range. In general, the overall acoustic attenuation provided by the earplug should be at least 10 dB more when the valve means are closed, compared to the case when the valve means are open.

The active unit may comprise an acoustic output transducer and means for producing audio signals for the output transducer, with the output transducer being acoustically connected to the sound output opening of the shell via the sound passage when the active unit is connected to the shell. The means for producing audio signals for the output transducer may comprise a microphone included within the active unit for sensing ambient sound and/or an interface for wireless connection with a remote audio signal source, such as a remote microphone. In both cases the active unit provides for an active hearing protection function to the earplug by enabling communication, in particular speech communication, via the microphone and the output transducer while the earplug is worn by the user.

Alternatively or in addition, the active unit may comprise a microphone which is adapted to be acoustically connected to the sound output opening of the shell via the sound passage when the active unit is connected to the shell. In this case, the microphone may be used for in-situ attenuation measurements of the earplug when worn by the user. In addition, the active unit may comprise dosimeter means connected to the microphone for determining the actual sound exposure experienced by the user's ear. The dosimeter means may be adapted for comparing the determined actual sound exposure to regulations implemented in the dosimeter means in order to judge whether the sound exposure complies with the regulations.

Usually the active unit comprises an audio signal processing unit for processing input audio signals provided by the microphone sensing ambient sound into the output audio signals for the output transducer. If a remote microphone is provided, the interface for wireless connection may be a radio frequency interface, in particular a frequency modulated radio signal interface or a Bluetooth interface, an inductive interface or an infrared interface.

In general, the earplug may be designed such that the user not only has the choice to use the earplug with or without the active unit but in addition the user has the option to select between functionally different active units, for example, one with a microphone and an output transducer for providing for an active hearing protection function, and one with a microphone and dosimeter means for providing for a dosimeter and sound exposure monitoring function. Thereby the flexibility of the hearing protection system is further enhanced.

In general, it is possible and desirable to manufacture not only the shell by a layer-by-layer build-up process, but also the functional components integrated within the shell, such as the valve means, whereby the manufacturing process can be significantly simplified.

In the following, examples of the design of the means for connecting the active unit to the shell and the valve means will be illustrated by reference to the drawings.

In general, the connecting means may be adapted for clipping, screwing or bayonet coupling the active unit to the shell. However, also any other quickly detachable connection may be used.

Figure 1B:
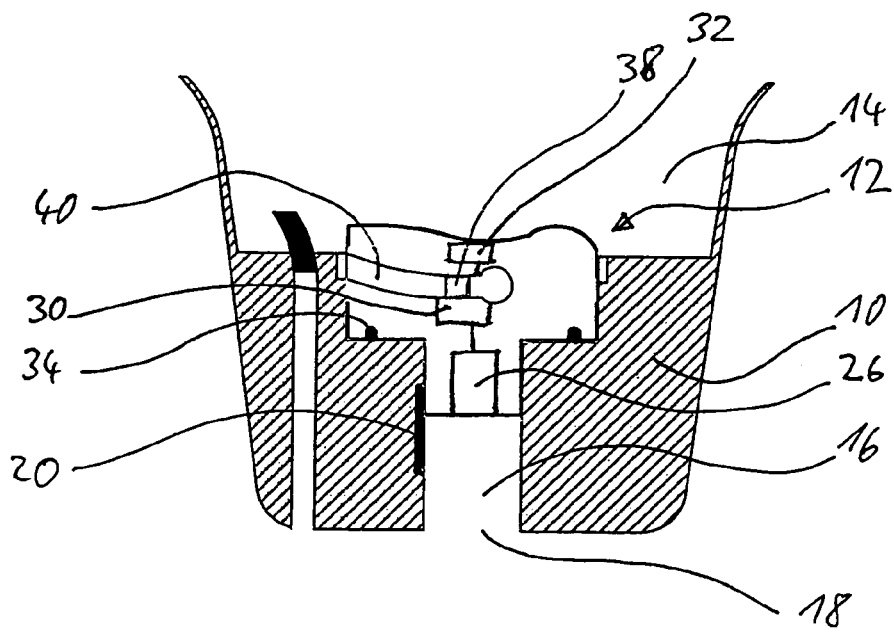

FIGS. 1a and 1b show an example where an active unit 12 is connected to a shell 10 by a bayonet coupling mechanism. In all Figures, only the distal portions of the shell 10 and the active unit 12 are shown, with the distal end of the shell being located at the bottom of each Figure. The shell 10 comprises an outer cavity 14 forming an outer opening into which the active unit 12 can be inserted for being connected to the shell 10. The outer cavity 14 is connected at its distal end to a sound passage 16 which extends between the outer cavity 14 and an inner sound output opening 18 provided at the distal end of the shell 10.

Within the sound passage 16 a valve member 20 is provided which is designed as a lid which is adapted to be tilted from a closed position, in which the lid 20 extends over the entire cross-section of the sound passage 16 (see FIG. 1a), into an open position in which the lid 20 exposes the sound passage 20 (see FIG. 1b). The dashed lines in FIG. 1a indicate an intermediate position of the lid 20. In the closed position, the lid 20 serves to acoustically close the sound passage 16 regarding the outer cavity 14.

In addition to the sound passage 16 the shell 10 may comprise a sound channel 22 extending from the outer cavity 14 to the distal end of the shell 10 which is acoustically closed by a passive filter element 24. The filter element 24 is provided for achieving a defined frequency dependent acoustic attenuation by the shell 10, whereby, for example, speech frequencies may be attenuated less than high frequency noise.

The active unit 12 comprises an acoustic output transducer 26, i.e. a speaker, at its distal end, which distal end is formed as an axial protection 28 adapted to move the lid 20 from the closed position shown in FIG. 1a into the open position shown in FIG. 1b, when the active unit 12 is connected to the shell 10. The lid 20 is biased towards the closed position of FIG. 1a in order to acoustically close the sound passage 16 when the active unit 12 is removed from the shell 10. In the position of FIG. 1b, wherein the active unit 12 is connected to the shell 10, the output transducer 26 is acoustically connected to the inner sound outlet opening 18 via the open sound passage 16.

The active unit 12 further comprises an audio signal processing unit 30 which processes input audio signals received from a microphone 32 into output audio signals for the output transducer 26.

The shell 10 is provided with a sealing lip 34 adapted for engagement with a mating groove 36 at the active unit 12 in order to seal the outer end of the sound passage 16 regarding the outer cavity 14 and hence regarding the environment around the user when the active unit 12 is connected to the shell 10.

The active unit 12 further comprises radial projections 38 which are adapted for engagement with mating slots 40 provided at the shell 10. The slots 40 and the radial projections 38 are designed for providing for a bayonet-like engagement between the active unit 12 and the shell 10 when the active unit 12 is inserted into the shell 10 and is slightly rotated against the shell 10.

When the active unit 12 is removed from the shell 10 again the lid 10 will automatically move into the closed position shown in FIG. 1a due to the biasing forces.

Figure 2:
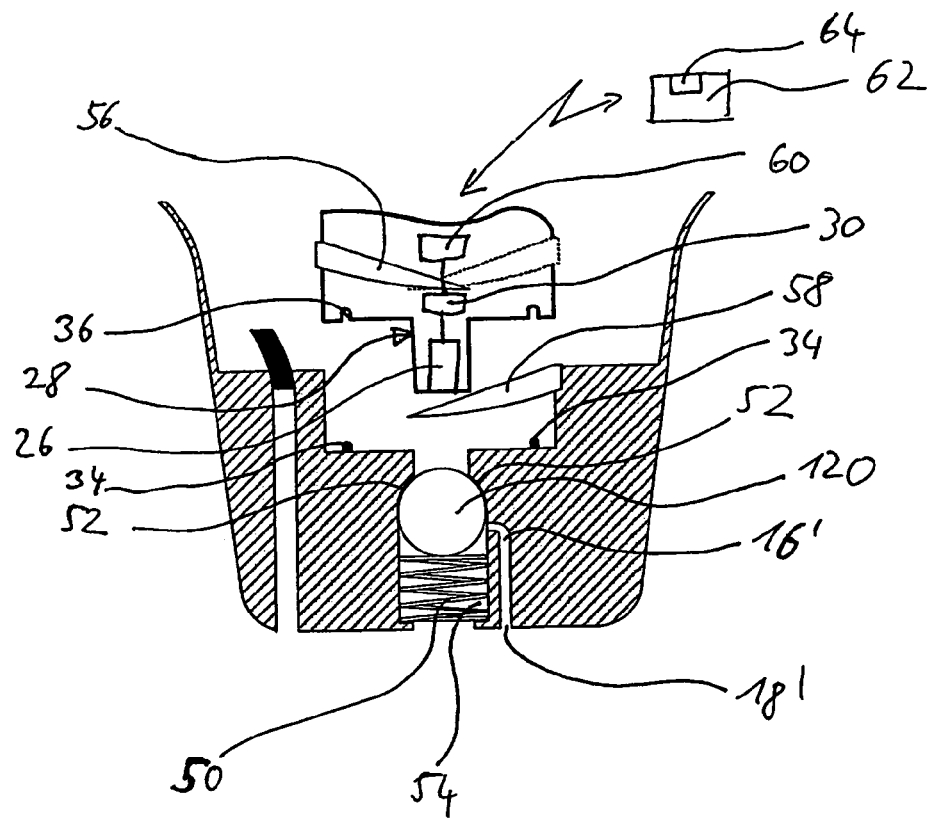
FIG. 2 to FIG. 4 show views, similar to that of FIG. 1a, of modified embodiments of the invention.

In FIG. 2 a modified embodiment is shown in which the bayonet mechanism of FIGS. 1a and 1b is replaced by a screw mechanism and wherein the lid-like valve member 20 is replaced by a ball-like valve member 120.

In general, FIG. 2 is an example of the case in which the acoustic valve comprises a valve member which is axially movable within the sound passage between the closed position and the open position, with the valve member being biased towards the closed position by a spring element which is arranged distal from the valve member.

In the embodiment shown in FIG. 2, a spring element 50 rests against the distal end of the shell 10 in order to bias the ball 120 outwardly against a spherically shaped surface 52 of the sound passage 16 in order to acoustically close the sound passage 16 when the active 12 is not connected to the shell 10. The spring element 50 is located within an inner cavity 54 of the shell. In the embodiment of FIG. 2 the sound passage 16 comprises a portion 16' which is angled regarding the axial direction of the shell 10 and which is located distal from the closed position of the ball 120. In the embodiment of FIG. 2 the angled portion 16' of the sound passage 16 extends to an outer sound outlet opening 18' at the distal end of the shell 10, with the angled portion 16' thus bypassing the inner cavity 54 in which the spring element 50 is located.

When the active unit 12 is inserted into the shell 10, the axial protection 28 will axially move the ball 120 from the closed position of FIG. 2 towards the distal end of the shell 10 against the biasing force of the spring element 50, thereby reaching the open position in which the centre of the ball 120 is located distal from the point where the angled portion 16' starts, thereby acoustically opening the sound passage 16, 16' extending from the outer cavity 14 towards the inner sound outlet opening 18'.

In the embodiment of FIG. 2, the active unit 12 and the shell 10 are provided with mating threads 56, 58 in order to allow the active unit 12 to be screwed into the shell 10 for connecting the active unit 12 to the shell 10. Preferably the thread is so steep that rotation corresponding to from a half turn to a full turn is sufficient for achieving engagement between the active unit 12 and the shell 10.

A further difference between the embodiment of FIGS. 1a and 1b and FIG. 2 is that in the embodiment of FIG. 2 the internal microphone 32 of the active unit 12 is replaced by an interface 60 adapted for wireless communication with a remote audio signal source 62. The remote audio signal source 62 preferably comprises a microphone 64 in order to allow for wireless communication between the person using the earplug comprising the shell 10 and the active unit 12 and a second person using the external audio source 62 with the external microphone 64. The interface 60 may be, for example, a frequency modulated radio frequency interface or a Bluetooth interface.

Figure 3:
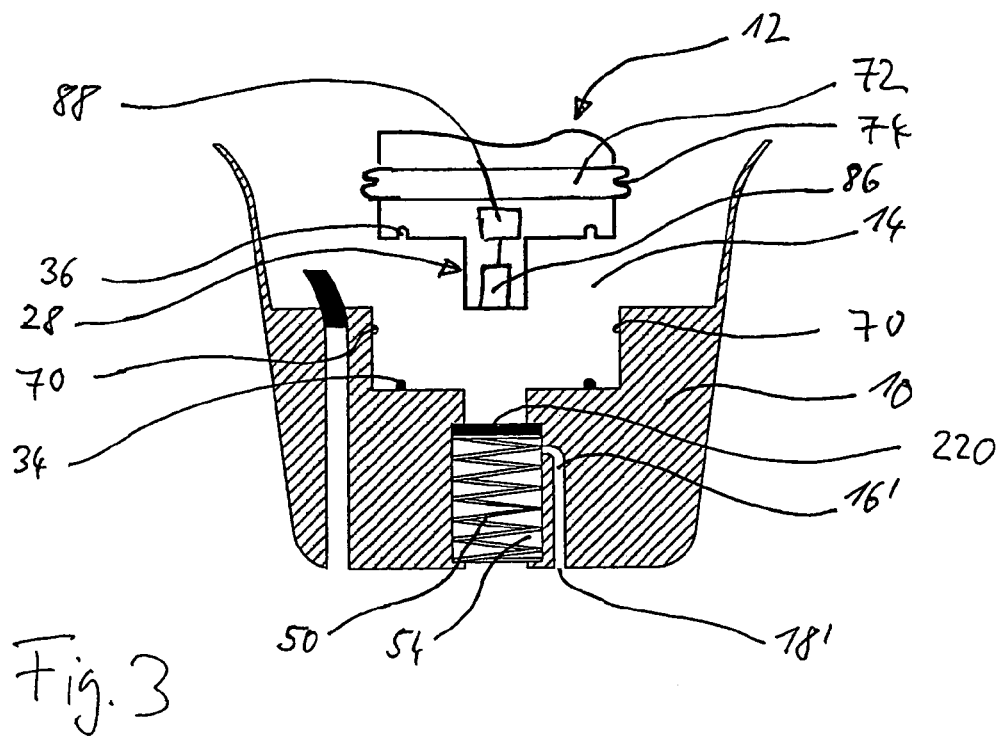

In the embodiment of FIG. 3 the ball 120 is replaced by a valve plate 220 which is located in the closed position proximal from the point where the angled portion 16' of the sound passage 16 starts, while the plate 220 is located in the open position proximal from that point in order to open the sound passage 16, 16' from the outer cavity 14 to the inner sound outlet opening 18'. In the closed position the valve plate 220 is biased by the spring element 50 against an axially oriented surface of the sound passage 16.

Further, the embodiment of FIG. 3 is an example for a clipping or snap-in mechanism for connecting the active unit 12 with the shell 10. Such mechanism may be generally achieved by providing either the active unit 12 or the shell 10 with a radially movable or resilient element adapted to engage a mating element provided at the counterpart, i.e. the shell 10 or the active unit 12, respectively.

More specifically, the embodiment of FIG. 3 is an example in which the shell 10 is provided with a rigid radially projecting projection 70, while the active unit 12 is provided with a soft lip 72 comprising a circumferential groove 74 into which the projections 70 of the shell 10 will engage when the active unit is axially pressed into the outer cavity 14 of the shell 10.

Figure 4:
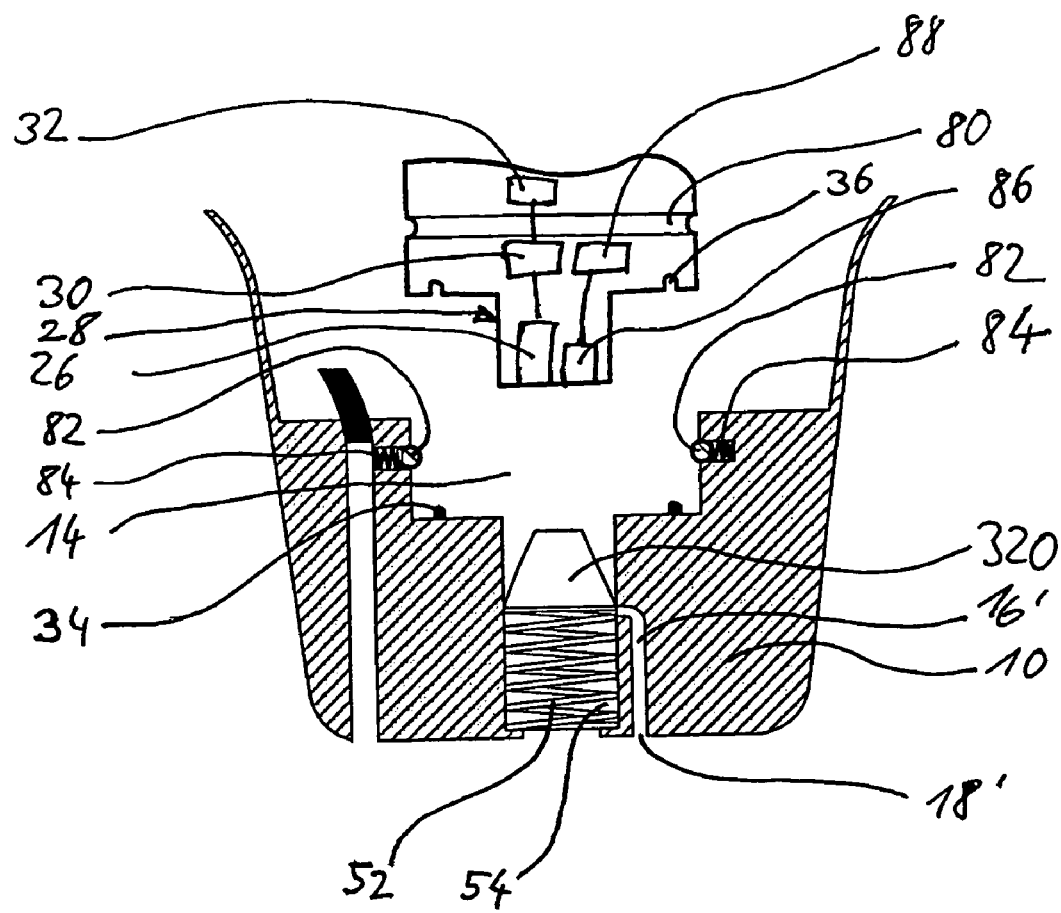

In the embodiment of FIG. 4 a modification of the clipping/snap-in mechanism is shown wherein the resilient lip 72 is replaced by a circumferential groove 80 provided at the outer surface of the active 12 and wherein the rigid projections 70 of the shell 10 are replaced by radially movable elements 82 which are radially biased towards the centre of the shell 10 by spring elements 84. In the example shown in FIG. 4 the engagement elements 84 are balls.

Further, in the embodiment of FIG. 4 the valve plate 220 is replaced by a conical body 320 which is tapered towards its outer end while its distal end fills the entire cross-section of the sound passage 16. In the closed position shown in FIG. 4 the distal end of the valve body 320 is located proximal from the point where the angled portion 16' of the sound passage 16 starts, while in the open position the valve body 320 is forced into the distal direction by the axial projection 28 of the active unit 12 so far that the distal end of the valve body 320 is located distal from the point where the angled portion 16' of the sound passage 16 starts, so that an acoustic connection between the outer cavity 14 and the inner sound outlet opening 18' via the sound passage 16, 16' is opened.

In the embodiment of FIG. 4 the active unit is provided with a distal microphone 86 which may be present alternatively or in addition to an output transducer 26. The distal microphone 86 may serve for performing in-situ sound attenuation measurements when the shell 10 is worn within the user's ear canal. Alternatively or in addition the distal microphone 86 may be connected to a digital data processing unit 88 which may serve as a dosimeter for determining and recording the actual sound exposure experienced by the user when wearing the earplug. In addition, the unit 88 may serve to compare the determined sound exposure to regulations implemented in the unit 88 in order to judge whether the determined sound exposure complies with the regulations, whereby a corresponding alarm signal may be output, i.e. an alarm sound or synthetic speech, if the regulations are infringed.

In FIG. 3 an example of an active unit 12 is shown which includes only a distal microphone 86 and a digital data processing unit 88 serving as a dosimeter.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A hearing protection earplug comprising a shell to be worn at least in part in a user's ear canal, said shell being adapted to provide for a mechanical acoustic attenuation of at least 10 dB averaged over an audible frequency range when worn by said user, an active unit comprising at least one of an acoustic output transducer and a microphone and means for detachably connecting said active unit to said shell, wherein said shell comprises a sound passage extending between an outer opening of said shell and an inner sound output opening at a distal end of said shell and comprising valve means which are moveable, upon connecting said active unit to said shell, from a closed position in which said valve means acoustically close said sound passage into an open position in which said valve means acoustically open said sound passage, said valve means being biased towards said closed position in order to acoustically close said sound passage when said active unit is removed from said shell, and wherein said at least one of an output transducer and a microphone is acoustically connected to said sound output opening via said sound passage when said active unit is connected to said shell.

2. A hearing protection earplug comprising a shell to be worn at least in part in a user's ear canal, said shell being adapted to provide for a mechanical acoustic attenuation of at least 10 dB averaged over the audible frequency range when worn by said user, an active unit comprising a microphone, and means for detachably connecting said active unit to said shell, wherein said shell comprises a sound passage extending between an outer opening of said shell and an inner sound output opening at a distal end of said shell and comprising valve means which are moveable, upon connecting said active unit to said shell, from a closed position in which said valve means acoustically close said sound passage into an open position in which said valve means acoustically opens said sound passage, said valve means being biased towards said closed position in order to acoustically close said sound passage when said active unit is removed from said shell, and wherein said microphone is acoustically connected to said sound output opening via said sound passage when said active unit is connected to said shell.

3. The earplug of claim 1, wherein said connecting means comprise sealing means for sealing the outer end of said sound passage regarding the environment around said user by engagement with said active unit.

4. The earplug of claim 1, wherein said connecting means are adapted for clipping, screwing or bayonet coupling said active unit to said shell.

5. The earplug of claim 1, wherein said connecting means are adapted for clipping said active unit to said shell and wherein one of said active unit and said shell comprises an element selected from the group consisting of a radially movable element and a resilient element, said element being adapted to engage a mating element provided at the other one of said active unit and said shell.

6. The earplug of claim 5, wherein said element is a radially movable element and is biased radially towards a center of said shell.

7. The earplug of claim 1, wherein said shell comprises an outer cavity into which said active unit is to be inserted.

8. The earplug of claim 1, wherein said valve means are adapted to provide in said closed position for an acoustic attenuation of at least 10 dB averaged over an audible frequency range.

9. The earplug of claim 1, wherein said valve means comprise a lid which is adapted to be tilted, upon connecting said active unit to said shell, from said closed position in which said lid extends over the entire cross section of said sound passage into said open position in which said lid exposes said sound passage.

10. The earplug of claim 1, wherein said active unit comprises a projection for moving said valve means, upon connecting said active unit to said shell, from said closed position to said open position.

11. The earplug of claim 10, wherein said valve means comprise a valve member which is axially movable within said sound passage by said projection between a first axial position in which said valve member acoustically closes said sound passage and a second axial position in which said valve member acoustically opens said sound passage.

12. The earplug of claim 11, wherein said valve member is biased towards said first axial position by a spring element arranged at least in part within said sound passage.

13. The earplug of claim 12, wherein said spring element is arranged distal from said valve member.

14. The earplug of claim 11, wherein said valve member is adapted to rest in said first axial position against a surface of said sound passage for acoustically closing said sound passage.

15. The earplug of claim 11, wherein said valve member is selected from the group consisting of a ball and a plate.

16. The earplug of claim 11, wherein said sound passage comprises a portion which is angled regarding the axial direction of said shell and which is located distal from said first position of said valve member.

17. The earplug of claim 1, further comprising means for producing audio output signals, said means for producing audio output signals comprising a remote microphone for converting ambient sound into input audio signals and wherein an audio signal processing unit is provided for processing said input audio signals into said output audio signals for said output transducer.

18. The earplug of claim 17, wherein said audio signal processing unit comprises an interface for wireless connection with said remote microphone.

19. The earplug of claim 18, wherein said interface is selected from the group consisting of a radio frequency interface, an inductive interface and an infrared interface.

20. The earplug of claim 19, wherein said interface is a Bluetooth interface.

21. The earplug of claim 17, wherein said active unit comprises dosimeter means for determining, by said microphone, a sound exposure of said user.

22. The earplug of claim 21, wherein said dosimeter means are adapted for comparing said determined sound exposure to regulations implemented in said dosimeter means in order to judge whether said sound exposure complies with said regulations.

23. The earplug of claim 1, wherein said shell has an outer surface individually shaped according to the measured inner shape of the user's outer ear and ear canal.

24. The earplug of claim 23, wherein said shell has an elasticity of from shore D-85 to shore D-65.

25. The earplug of claim 24, wherein said shell is made of polyamide.

26. The earplug of claim 19, wherein said interface is a frequency modulated radio signal interface.

27. A use of a hearing protection earplug according to claim 1, comprising:

connecting said active unit to said shell by engaging said connecting means, inserting said earplug at least in part into said user's ear canal, removing said earplug from said user's ear canal, disconnecting said active unit from said shell by disengaging said connecting means, and inserting said earplug at least in part into said user's ear canal.

28. The use of claim 27, further comprising: removing said earplug from said user's ear canal, connecting a further active unit which is functionally different from said active unit to said shell by engaging said connecting means, and inserting said earplug at least in part into said user's ear canal.

29. A hearing protection system comprising a shell to be worn at least in part in a user's ear canal, said shell being adapted to provide for a mechanical acoustic attenuation of at least 10 dB averaged over an audible frequency range when worn by said user, a plurality of functionally different active units comprising at least one of an acoustic output transducer and a microphone and means for detachably connecting a selected one of said active units to said shell, wherein said shell comprises a sound passage extending between an outer opening of said shell and an inner sound output opening at a distal end of said shell and comprising valve means which are moveable, upon connecting said selected one of said active units to said shell, from a closed position in which said valve means acoustically close said sound passage into an open position in which said valve means acoustically open said sound passage, said valve means being biased towards said closed position in order to acoustically close said sound passage when said selected one of said active units is removed from said shell, and wherein said at least one of an output transducer and a microphone is acoustically connected to said sound output opening via said sound passage when said selected one of said active units is connected to said shell.

30. A hearing protection system comprising a shell to be worn at least in part in a user's ear canal, said shell being adapted to provide for a mechanical acoustic attenuation of at least 10 dB averaged over an audible frequency range when worn by said user, a plurality of functionally different active units comprising a microphone, and means for detachably connecting a selected one of said active units to said shell, wherein said shell comprises a sound passage extending between an outer opening of said shell and an inner sound output opening at a distal end of said shell and comprising valve means which are moveable, upon connecting said selected one of said active units to said shell, from a closed position in which said valve means acoustically close said sound passage into an open position in which said valve means acoustically open said sound passage, said valve means being biased towards said closed position in order to acoustically close said sound passage when said selected one of said active units is removed from said shell, and wherein said microphone is acoustically connected to said sound output opening via said sound passage when said selected one of said active units is connected to said shell.

31. Method for manufacturing a hearing protection earplug comprising:

providing a shell to be worn at least in part in a user's ear canal, said shell being adapted to provide for a mechanical acoustic attenuation of at least 10 dB averaged over an audible frequency range when worn by said user, and said shell comprising a sound passage extending between an outer opening of said shell and an inner sound output opening at a distal end of said shell; and providing an active unit comprising at least one of an acoustic output transducer and a microphone means for producing output audio signals for said output transducer, said active unit being adapted for being detachably connected to said shell;

said shell comprising valve means which are moveable, upon connecting said active unit to said shell, from a closed position in which said valve means acoustically close said sound passage into an open position in which said valve means acoustically open said sound passage, said valve means being biased towards said closed position in order to acoustically close said sound passage when said active unit is removed from said shell, and said an output transducer and a microphone being acoustically connected to said sound output opening via said sound passage when said active unit is connected to said shell;

wherein said shell including said valve means is manufactured by an additive layer-by-layer build-up process.

32. Method for manufacturing a hearing protection earplug comprising:

providing a shell to be worn at least in part in a user's ear canal, said shell being adapted to provide for a mechanical acoustic attenuation of at least 10 dB averaged over an audible frequency range when worn by said user, and said shell comprising a sound passage extending between an outer opening of said shell and an inner sound output opening at a distal end of said shell; and providing an active unit comprising a microphone, said active unit being adapted for being detachably connected to said shell;

said shell comprising valve means which are moveable, upon connecting said active unit to said shell, from a closed position in which said valve means acoustically close said sound passage into an open position in which said valve means acoustically open said sound passage, said valve means being biased towards said closed position in order to acoustically close said sound passage when said active unit is removed from said shell, and said microphone being acoustically connected to said sound output opening via said sound passage when said active unit is connected to said shell;

wherein said shell including said valve means is manufactured by an additive layer-by-layer build-up process.

* * * * *